United States Patent [19]

Lippert et al.

[11] Patent Number: 5,705,683
[45] Date of Patent: Jan. 6, 1998

[54] CARBONYLATION OF OLEFINS

[75] Inventors: Ferdinand Lippert, Bad Dürkheim; Arthur Höhn, Kirchheim; Martin Schäfer, Ludwigshafen; Leopold Hupfer, Friedelsheim, all of Germany

[73] Assignee: BASF Aktiengesellschaft, Ludwigshafen, Germany

[21] Appl. No.: 765,739

[22] PCT Filed: Jul. 3, 1995

[86] PCT No.: PCT/EP95/02560

§ 371 Date: Jan. 13, 1997

§ 102(e) Date: Jan. 13, 1997

[87] PCT Pub. No.: WO96/02487

PCT Pub. Date: Feb. 1, 1996

[30] Foreign Application Priority Data

Jul. 13, 1994 [DE] Germany ............... P 44 24 710.9

[51] Int. Cl.$^6$ .................... C07C 51/14; C07C 51/56; C07C 67/38
[52] U.S. Cl. .................... 562/522; 562/890; 562/895; 560/233
[58] Field of Search ................... 562/522, 890, 562/895; 560/233

[56] References Cited

U.S. PATENT DOCUMENTS

| | | | |
|---|---|---|---|
| 2,658,075 | 11/1953 | Reppe et al. | 562/522 |
| 2,768,968 | 10/1956 | Reppe et al. | 562/522 |
| 3,717,670 | 2/1973 | Schultz | 562/522 |
| 4,431,593 | 2/1984 | Jenck | 560/233 |
| 4,625,055 | 11/1986 | Rizkalla | 562/406 |

FOREIGN PATENT DOCUMENTS

| | | |
|---|---|---|
| 329 252 | 8/1989 | European Pat. Off. |
| 495 547 | 7/1992 | European Pat. Off. |
| 43-7928 | 3/1968 | Japan. |
| 630279 | 10/1949 | United Kingdom. |
| 1063617 | 3/1979 | United Kingdom. |

*Primary Examiner*—José G. Dees
*Assistant Examiner*—Rosalynd A. Keys
*Attorney, Agent, or Firm*—Keil & Weinkauf

[57] ABSTRACT

The process for carbonylating olefins with carbon monoxide in the presence of water, an alcohol or a carboxylic acid and a halogen-free catalyst comprises using a catalyst comprising nickel or a nickel compound and at least one of the metals of the group consisting of chromium, molybdenum, tungsten, rhenium, ruthenium, osmium, rhodium, iridium, palladium, platinum, silver and gold, or a compound of these metals.

5 Claims, No Drawings

CARBONYLATION OF OLEFINS

This Application is a 371 of PCT/EP95/02560 filed Jul. 3, 1995.

The present invention relates to an improved process for carbonylating olefins with carbon monoxide in the presence of water, an alcohol or a carboxylic acid and a halogen-free catalyst.

Weissermel et al. describe in Industrielle Organische Chemie, 1978, 2nd edition, Verlag Chemie, p. 132 the carbonylation of olefins by the Reppe process, for example the synthesis of propionic acid from ethylene, carbon monoxide and water in the presence of catalysts. The catalyst used is nickel propionate, which is converted under the reaction conditions into nickel tetracarbonyl. A high conversion of the carbon monoxide is achieved only at high pressures (200–240 bar) and temperatures (270°–320° C.). These reaction conditions require a high technical outlay in the construction of suitable reactors and, owing to the corrosivity of the product under the reaction conditions, special and costly materials of construction.

GB-A 1 063 617 teaches the carbonylation of olefins with nickel and cobalt catalysts in the presence of boric acid. Again high pressures and temperatures are required.

Carbonylations of olefins can be carried out with noble metal catalysts at pressures of about 100 bar. For instance, EP-A 495 547 discloses catalysts consisting of a palladium source and bidentate phosphine ligands. However, catalysts of this type are frequently inactivated after a short reaction time by deposition of metallic palladium; more particularly, the phosphine ligands used are not thermally stable under the desired reaction conditions.

EP-A 329 252 relates to a catalyst system for the carbonylation of olefins, which comprises a ruthenium component and also an oxygen compound of phosphorus, antimony, arsenic, molybdenum or tungsten. However, the activity of such catalysts is low, so that they are little suited for use on an industrial scale.

It is an object of the present invention to provide a process for carbonylating olefins which avoids the above-mentioned disadvantages.

We have found that this object is achieved by the above-indicated process, which comprises using a catalyst comprising nickel or a nickel compound and at least one of the metals of the group consisting of chromium, molybdenum, tungsten, rhenium, ruthenium, osmium, rhodium, iridium, palladium, platinum, silver and gold, or a compound of these metals.

The following reaction equation illustrates the process of the present invention taking the example of the conversion of ethylene into propionic acid:

Suitable starting materials for the process of the present invention are aliphatic and cycloaliphatic alkenes with, preferably, 2–50, particularly preferably 2–7, carbon atoms. Examples which may be mentioned are ethylene, propylene, isobutene, 1-butene, 2-butene and the isomers of pentene and hexene and also cyclohexene, of which ethylene is preferred.

These olefins are reacted with water to prepare carboxylic acids, with alcohols to prepare carboxylic esters, and with carboxylic acids to prepare carboxylic anhydrides.

The alcohols comprise aliphatic and cycloaliphatic compounds with, preferably, 1–20 carbon atoms, particularly preferably with 1–6 carbon atoms, such as methanol, ethanol, n-propanol, isopropanol, isobutanol, tert-butanol, stearyl alcohol, diols such as ethylene glycol, 1,2-propanediol and 1,6-hexanediol, and also cyclohexanol. If diols are reacted, mono- and diesters may be obtained depending on the chosen stoichiometric ratios, diesters being prepared by employing the diol and the olefin in a molar ratio of about 1:2 and the monoesters being prepared by employing the diol in excess.

Carbonylation of the olefin in the presence of anhydrous carboxylic acids gives carboxylic anhydrides. The carboxylic anhydrides which can be formed are preferably symmetrical, but can also be asymmetrical, depending on the choice of carboxylic acid.

The starting compounds mentioned are reacted with carbon monoxide which can be employed in pure form or diluted with inert gases such as nitrogen or argon.

The molar ratios of olefin and water, alcohol or carboxylic acid can vary within wide limits, but generally an at least equimolar amount of water, alcohol or carboxylic acid is used, based on the olefin. A large excess of water can be used in particular in the preparation of carboxylic acids, eg. 2–10 mol of water per mole of olefin.

Similarly, the ratio of olefin to carbon monoxide can be varied within wide limits, for example within the range from 5:1 to 1:5 mol of olefin per mole of carbon monoxide.

The catalysts used in the process of the present invention are combinations of nickel and at least one further metal or compounds thereof. In order for the active compounds of nickel to form, the reaction mixture is advantageously admixed with nickel compounds soluble therein, for example acetate, propionate, acetylacetonate, hydroxide or carbonate or mixtures thereof. Particular preference is given to adding the nickel component for the preparation of carboxylic acids in the form of carboxylic acid salts of the carboxylic acids formed in the course of the reaction. However, it is also possible to add nickel metal to the reaction mixture. It is also possible to use nickel on inert carriers such as activated carbon.

The further catalyst component used is at least one of the metals, or a compound thereof, from the group consisting of Cr, Mo, W, Re, Ru, Os, Rh, Ir, Pd, Pt, Ag and Au, of which Rh and Pd are preferred and Ru and Pt are particularly preferred. The metals can be introduced into the reaction solution for example as salts, as indicated above for nickel, ie. as acetates, propionates, acetylacetonates, hydroxides or carbonates. It is also possible to use carbonyl compounds, especially chromium hexacarbonyl, molybdenum hexacarbonyl, tungsten hexacarbonyl, dirhenium decacarbonyl, triruthenium decacarbonyl, triosmium dodecacarbonyl and carbonyl compounds which carry further ligands such as rhodium dicarbonyl acetylacetonate or metal compounds stabilized by donor ligands such as phosphines, arsines and nitrogen bases and also olefins. Platinum can also be used in the form of dibenzalacetoneplatinum. Ruthenium is preferably used in the form of the acetylacetonate. The metals are present in the reaction mixture in solution or suspension, depending on the solubilities. The metals or metal compounds can also be used on organic or inorganic inert carriers such as activated carbon, graphite, alumina, zirconia and silica, eg. Pt on activated carbon or Pd on activated carbon.

The molar ratio of nickel to the other metal is generally within the range from 1:10 to 10,000:1, preferably from 1:1 to 500:1. The proportion of catalytically active metals in the reaction solution is generally from 0.01 to 5% by weight, calculated as metal.

The reaction can be carried out with or without a solvent. Suitable solvents include such as acetone, ethers such as dioxane, dimethoxyethane, or tetraethylene glycol dimethyl ether, aprotic polar solvents such as N-methylpyrrolidone, dimethylpropylene urea and aromatic hydrocarbons such as toluene and xylene. A carboxylic acid can be prepared in water as solvent, but it is preferable to carry out the preparation of a carboxylic acid in said carboxylic acid containing from 10 to 90% by weight of water. Similarly, the esters are preferably prepared in the respective alcohol as solvent. Carboxylic anhydrides are preferably prepared in anhydrous carboxylic acids.

The reaction is generally carried out at from 100° to 300° C., preferably at from 170° to 250° C., and pressures from 30 to 150 bar, preferably from 75 to 120 bar.

The starting compounds of olefin, water, alcohol/carboxylic acid and catalyst can be mixed before the reaction in a reactor in the presence or absence of a solvent. The mixture can then be heated to the reaction temperature. The reaction pressure can be set by injecting carbon monoxide or, if short-chain olefins are used, by injecting a mixture of the olefin in question and carbon monoxide.

The reaction is generally complete after 0.5–3 h. It can be carried out continuously or batchwise in reactors such as tanks, bubble columns or tubular reactors.

To isolate the products, the exit stream from the reaction is preferably decompressed. Nickel carbonyl is then expelled from the liquid by passing an inert gas such as nitrogen through the liquid. Nickel carbonyl can be separated from the inert gas and worked up to a nickel compound which can be returned to the reaction. The liquid phase of the exit stream, which contains soluble or insoluble catalyst constituents as well as the product, is filtered, if necessary, and then worked up by distillation to isolate the product, if necessary after a subsequent precision distillation. The catalyst-containing distillation residue is returned to the reaction. In the catalyst constituents filtered off prior to the distillation can similarly be returned after an appropriate workup.

The process of the present invention makes it possible to produce the products in a high space-time yield with high selectivity under moderate reaction conditions.

established with a mixture of 50% by volume of ethylene and 50% by volume of CO and maintained by further injection. After 2 h, the system was decompressed and the exit stream was analyzed by titrimetry and gas chromatography. The results are summarized in the following Table:

| Example | Catalyst [nmol] | | STY | Selectivity [%] | | |
| --- | --- | --- | --- | --- | --- | --- |
| | Ni | Ru | [g PA/(1·h)] | PA | PD | DEK |
| 1 | 16.99 | 0.075 | 175 | 86 | 1.1 | 1.6 |
| 2 (Comparison) | 17.07 | — | 9 | 88 | 0 | 3.6 |
| 3 (Comparison) | — | 17.07 | 17 | 28 | 0 | 4.2 |

STY = space-time yield
PA = propionic acid
PD = propionaldehyde, by-product
DEK = diethyl ketone, by-product Example 1, using both Ni and Ru according to the present invention, gave for the same number of moles of catalyst metal distinctly higher space-time yields and selectivities than the runs using in each case only one metal compound as catalyst.

Continuous preparation of the propionic acid

A mixture of propionic acid, water and nickel propionate plus ruthenium acetylacetonate was continuously reacted at 200° C. and 100 bar with a mixture of 50% by volume of ethylene and 50% by volume of CO. With an average residence time RT within the range from 0.5 to 1 h, reaction mixture was continuously removed and analyzed. The following table indicates the results:

| Example | Starting materials [% by weight] | | | | RT [h] | Ethene conversion [%] | PA yield [%] | PA sel. [%] | STY [g/(1·h)] |
| --- | --- | --- | --- | --- | --- | --- | --- | --- | --- |
| | PA | H₂O | Ni | Ru | | | | | |
| 3 | 59.2 | 39.4 | 0.41 | 0.10 | 0.75 | 60 | 52 | 86 | 132 |
| 4 | 39.5 | 59.9 | 0.49 | 0.10 | 1.00 | 87 | 69 | 80 | 100 |
| 5 | 59.4 | 40.0 | 0.49 | 0.10 | 0.75 | 77 | 62 | 80 | 159 |
| 6 | 58.8 | 40.1 | 1.01 | 0.05 | 0.75 | 80 | 60 | 75 | 269 |
| 7 | 58.8 | 40.1 | 1.00 | 0.10 | 0.50 | 86 | 60 | 71 | 287 |
| 8 | 39.2 | 59.8 | 1.00 | 0.05 | 0.75 | 85 | 58 | 68 | 240 |

PA sel. = selectivity of the reaction for propionic acid

The products of the process of the present invention are used as intermediates for a multiplicity of compounds, for example monomers with carboxylate groups, as preservatives (propionic acid) and as solvents, for example for coatings.

EXAMPLES

Batchwise preparation of propionic acid

An autoclave was charged with a catalyst (Ni in the form of nickel propionate, Ru in the form of ruthenium acetylacetonate) and a mixture of 60 g of propionic acid and 40 g of water. At 200° C. a pressure of 100 bar was

EXAMPLES

Batchwise preparation of propionic acid

An autoclave was charged with the nickel catalyst (in the form of nickel propionate), the co-catalyst (see table) and a mixture of 60 g of propionic acid and 40 g of water. At 200° C. a pressure of 100 bar was established with a mixture of 50% by volume of ethylene and 50% by volume of CO and maintained by further injection. After 2 h, the system was decompressed and the exit stream was analyzed by titrimetry and gas chromatography. The results are summarized in the following table:

| Example | Cocatalyst | Catalysts [mmol] Ni | Catalysts [mmol] Cocatalyst | STY [g PA/(1 · h)] | Selectivity [%] PA | Selectivity [%] PD | Selectivity [%] DEK | Selectivity [%] $C_2H_6$ |
| --- | --- | --- | --- | --- | --- | --- | --- | --- |
| 9 | Pt (5%)/C | 17 | 0.65 | 113 | 95 | 2.7 | 0 | 2.3 |
| 10 | Pt (5%)/C | — | 0.65 | 17 | 36 | 40.0 | 2.0 | 10.6 |
| Comparison 11 | — | 17 | — | 9 | 88 | 0 | 3.6 | 5.8 |
| Comparison 12 | Pt (5%)/C | 34 | 0.65 | 119 | 97 | 1.4 | 0 | 1.5 |
| 13 | Pt (5%)/$ZrO_2$ | 17 | 0.65 | 64 | 89 | 2.7 | 0.9 | 5.5 |
| 14 | Pt (dba)$_2$ | 17 | 0.65 | 118 | 95 | 3.7 | 0 | 1.2 |
| 15 | Pt (acac)$_2$ | 17 | 0.52 | 83 | 87 | 4.4 | 3.3 | 5.8 |
| 16 | Pd (10%)/C (5 g) | 17 | 4.7 | 57 | 81 | 3.8 | 0.8 | 5.5 |
| 17 | Pd (3%)/Re (3%)/C | 17 | 0.7 Pd/0.4 Re | 91 | 89 | 2.2 | 0.8 | 5.5 |
| 18 | $Re_2$ (CO)$_{10}$*) | 17 | 0.2 | 85 | 96 | 0.2 | 0.6 | 3.2 |

*)length of run 8 h
STY = space-time yield
PA = propionic acid
PD = propionaldehyde, by-product
DEK = diethyl ketone, by-product
acac = acetylacetonate
dba = dibenzalacetone
C = activated carbon

We claim:

1. A process for carbonylating olefins with carbon monoxide in the presence of water, an alcohol or a carboxylic acid and a halogen-free catalyst, which comprises using a catalyst comprising nickel and ruthenium or nickel and platinum or a compound of these metals.

2. A process as claimed in claim 1, wherein the carbonylation is carried out at a temperature from 170° to 250° C. and at a pressure from 30 to 150 bar.

3. A process as claimed in claim 1, wherein ethylene is carbonylated in the presence of water to form propionic acid.

4. A process as claimed in claim 3, wherein the synthesis of propionic acid is carried out in a solvent comprising propionic acid with a water content from 10 to 90% by weight.

5. A process as claimed in claim 1, wherein ethylene is reacted in the presence of water-free propionic acid to form propionic anhydride.

* * * * *